(12) United States Patent
Müller

(10) Patent No.: US 10,253,288 B2
(45) Date of Patent: Apr. 9, 2019

(54) RECEPTACLE FOR ACCEPTING NUTRIENT MEDIA

(75) Inventor: Rolf Müller, Dossenheim (DE)

(73) Assignee: MERCK PATENT GMBH, Darmstadt (DE)

( * ) Notice: Subject to any disclaimer, the term of this patent is extended or adjusted under 35 U.S.C. 154(b) by 1538 days.

(21) Appl. No.: 12/526,200

(22) PCT Filed: Apr. 9, 2008

(86) PCT No.: PCT/DE2008/000589
§ 371 (c)(1),
(2), (4) Date: Aug. 6, 2009

(87) PCT Pub. No.: WO2008/141597
PCT Pub. Date: Nov. 27, 2008

(65) Prior Publication Data
US 2010/0093075 A1    Apr. 15, 2010

(30) Foreign Application Priority Data

May 24, 2007 (DE) .................. 10 2007 024 620
Jun. 11, 2007 (DE) .................. 10 2007 027 273

(51) Int. Cl.
C12M 1/22     (2006.01)
C12M 1/00     (2006.01)
C12M 3/00     (2006.01)

(52) U.S. Cl.
CPC ............ *C12M 23/10* (2013.01); *C12M 23/38* (2013.01); *C12M 23/46* (2013.01); *C12M 23/22* (2013.01)

(58) Field of Classification Search
CPC .......................... C12M 23/10; C12M 23/46
(Continued)

(56) References Cited

U.S. PATENT DOCUMENTS 3,055,808 A    9/1962   Henderson
3,158,553 A    11/1964  Carski
(Continued)

FOREIGN PATENT DOCUMENTS

DE    1 940 202    6/1966
DE    31 28 542    4/1982
(Continued)

OTHER PUBLICATIONS

International Preliminary Report on Patentability and Written Opinion for Appl. No. PCT/DE2008/000589 dated Dec. 7, 2009.
(Continued)

*Primary Examiner* — Jonathan M Hurst
(74) *Attorney, Agent, or Firm* — Alston & Bird LLP

(57) ABSTRACT

Disclosed is a receptacle for accepting nutrient media, especially for bacterial cultures. Said receptacle comprises a dish and a lid that covers the dish. The dish and the lid each have a circular bottom (dish bottom and lid bottom) and an annular wall (dish wall and lid wall) that projects from the bottom. One of the walls, preferably the lid wall, has an at least slightly larger internal diameter than the external diameter of the other wall, preferably the dish wall, such that one wall can be slid onto the other wall to close the dish. In order to be able to safely handle the receptacle, engaging means which prevent the dish and the lid from being accidentally released when the same are mutually engaged, are associated with the dish and the lid.

22 Claims, 5 Drawing Sheets

(58) Field of Classification Search
USPC .................................................. 435/305.4
See application file for complete search history.

(56) References Cited

U.S. PATENT DOCUMENTS

| | | | |
|---|---|---|---|
| 3,769,936 A * | 11/1973 | Swanson et al. | 119/6.5 |
| 4,675,298 A | 6/1987 | Brusewitz | |
| 5,021,351 A * | 6/1991 | Ervin | 435/305.1 |
| 5,348,885 A | 9/1994 | Labarthe | |
| 5,605,836 A | 2/1997 | Chen et al. | |
| 5,725,123 A | 3/1998 | Otto-Nagels | |
| 6,756,225 B2 * | 6/2004 | Bedingham et al. | 435/305.1 |
| 6,969,606 B2 * | 11/2005 | Minton | 435/288.3 |
| 7,273,750 B1 | 9/2007 | Olivier et al. | |
| 2001/0024821 A1 | 9/2001 | Potter | |
| 2004/0224382 A1 | 11/2004 | Olson, Jr. | |
| 2006/0240549 A1 | 10/2006 | Minton | |

FOREIGN PATENT DOCUMENTS

| | | |
|---|---|---|
| DE | 44 06 725 | 9/1995 |
| DE | 100 11 310 | 9/2001 |
| EP | 0 119 984 | 9/1984 |
| EP | 0 171 174 | 2/1986 |
| EP | 0 848 057 | 6/1998 |
| EP | 1 528 100 | 5/2005 |
| FR | 2 639 957 | 6/1990 |
| GB | 2 263 703 | 8/1993 |
| JP | 60-15302 B2 | 4/1985 |
| JP | 10-80268 | 3/1998 |
| JP | 2004-337079 | 12/2004 |

OTHER PUBLICATIONS

International Search Report for International Application No. PCT/DE2008/000589 completed Dec. 29, 2008.

* cited by examiner

Section A-A
M 2:1

Section C-C
M 2:1

Position: open

Section D-D
M 1:1

Position: closed

Section E-E
M 1:1

RECEPTACLE FOR ACCEPTING NUTRIENT MEDIA

BACKGROUND OF THE INVENTION

The invention relates to a receptacle for accepting nutrient media, these being understood to include nutrient solutions or nutrient substrates, for example, in particular for the cultivation of microorganisms, cell cultures, bacteria, etc. The receptacle comprises a dish and a cover which closes the dish. It is to be noted here that the cover may enclose the dish or engage in the dish. As a result, the dish and the cover are to be understood very generally as parts which engage in one another to form a more or less closed chamber. For simplification, reference will be made hereafter to the dish and the cover.

The dish and the cover each comprise a bottom implemented in the form of a circular surface (dish bottom and cover bottom), and a circular ring wall protruding from the bottom (dish wall and cover wall). One of the walls, preferably the cover wall, has an at least slightly larger inner diameter than the outer diameter of the other wall, preferably the dish wall, so that one wall may be slipped over the other (or vice versa) to close the dish.

Receptacles of the type under discussion are known under the name "Petri dish." This is understood as a flat, round, usually transparent glass or plastic dish having an overlapping cover. Such a dish is typically employed in biology or chemistry. It is used for cultivating microorganisms and is employed for establishing cell cultures.

Reference is made to DE 44 06 725 A1, solely for exemplary purposes, with regard to the receptacle forming the species from which a receptacle in the meaning of a Petri dish is known. A cover is used for closing the receptacle. The cover is normally slipped over the dish and/or over the dish wall. The handling of a receptacle closed in this way is problematic, however, because detachment of the dish and the cover cannot to be avoided when grasping the cover. Contaminants thus reach the interior of the receptacle or established cultures may get outside the receptacle. There is a danger of contamination.

Causing a clamping action between the dish and the cover by suitable design and dimensioning of the dish and the cover is already known from practice. If one wishes to generate a secure connection between the dish and the cover, a type of press fit must be implemented, which makes detaching the cover from the dish more difficult, if not even impossible. As a result, such a solution is only suitable in a limited way for the secure closing and opening of the receptacle.

The present invention is based on the object of designing and refining a receptacle for accepting nutrient media, in particular for cultivating microorganisms, cell cultures, and/or organisms, in such a way that secure handling is possible in particular with a closed receptacle. The danger of unintentional detachment of the cover from the dish is to be avoided as much as possible, intentional detachment of the cover from the dish having to be possible without great force application.

SUMMARY OF VARIOUS EMBODIMENTS

The preceding object is achieved according to the invention by the features of claim 1. Accordingly, the receptacle under discussion here is characterized in that engagement means are assigned to the dish and the cover, which prevent unintentional detachment of the cover from the dish upon mutual engagement.

According to the invention, it has been recognized that the clamping action between the dish and the cover which is known from practice is inadequate, on the one hand, and involves the danger that the cover will not be able to be detached from the dish because of a particularly strong clamping action, on the other hand. Thus, the invention has branched off from a conventional connection between the dish and the cover on the basis of a clamping action, namely on the basis of a press fit, and has selected a connection by engagement means, these engagement means being assigned to both the dish and also the cover. The engagement means are implemented and/or designed in such a way that upon mutual engagement of the engagement means, unintentional detachment of the cover from the dish is effectively avoided. If the engagement means are disengaged, the cover may be removed easily from the dish.

In regard to an embodiment of the receptacle having a simple design, it is advantageous if the engagement means are integral components of the dish, on the one hand, and the cover, on the other hand. The engagement means may be assigned to the cover wall and the dish wall. It is also conceivable that the engagement means are assigned to the cover wall, on the one hand, and to a peripheral outer boundary area of the dish, on the other hand. It is only essential that engagement means are assigned to both the dish and also the cover, which may be mutually engaged upon closing of the dish by the cover, so that unintentional detachment of the cover from the dish is prevented.

In a further advantageous way, the outer boundary area of the dish, which lies outside the dish because of the configuration and/or implementation of the dish wall, is used for the contact for the cover wall, specifically when the cover wall engages over the dish wall.

Accordingly, it is advantageous if the dish wall is implemented as offset inward from the outer boundary area, and if the boundary area lying outside the dish wall, preferably entirely on the outside, carries the engagement means. It is to be noted here that this exclusively relates to the mutual engagement of the engagement means which are assigned to both the dish and also the cover. Alternatively, a design of the dish and the cover is also possible in such a way that the dish wall overlaps the cover wall, so that the cover is insertable into the dish, i.e., into the area inside the dish wall. Mutual engagement of the engagement means is also possible in the context of such a design, so that the teaching according to the invention is also applicable in this regard.

It is noted hereafter, solely as representative for all conceivable design variants, that the cover overlaps the dish or the dish wall, although another implementation, which corresponds to the preceding statements, is conceivable. In a further advantageous way, the engagement means of the cover are implemented on the free boundary or close to the free boundary of the cover wall. The engagement means of the cover may be implemented as catch lugs, flanges, thread-like parts, combinations of different engagement means, or the like, which preferably protrude orthogonally outward from the cover wall. These engagement means are used for engaging in corresponding engagement means on the dish, the engagement means of the cover being able to be plugged, inserted, screwed, or introduced in another way into the engagement means of the dish.

The engagement means of the cover may concretely comprise at least one or more catch position, the catch position being understood to mean that the engagement means of the cover have—symmetrical or asymmetrical—reductions in cross-section, undercuts, material tapering, etc., which form and/or define the catch position in relation to the engagement means of the dish.

The engagement means of the dish are implemented corresponding to the design of the engagement means of the cover, namely to be able to accommodate the engagement means of the cover in a formfitting and/or friction-locked way. For this purpose, it is advantageous that the engagement means of the dish are implemented like clamps, flanges, threads, or in the meaning of various types of engagement to at least partially encompass and/or engage and/or overlap the engagement means of the cover. Furthermore, it is advantageous if the engagement means of the dish have at least one design measure for the clamping engagement of the engagement means of the cover. This may be a wedge face or another protrusion for clamping engagement.

A further embodiment of the teaching according to the invention is especially advantageous, to the effect that the engagement means of the dish are implemented in such a way that the engagement means of the cover may be engaged by rotating the cover in relation to the dish. It is conceivable that—in addition—sealing means act between the dish and the cover, for example, a sealing ring laid on the boundary area of the dish or the like.

It is especially advantageous if the engagement means of the cover have wedge faces of different heights and different inclinations, insertable approximately halfway from both sides having different clamping and sealing actions, so that the engagement means of the cover are insertable from both sides with different clamping and sealing actions. In the context of such a design, it is possible to position the cover or the engagement means of the cover to the left or right of the engagement means of the dish in each case and insert the engagement means of the cover in the engagement means of the dish—from the left or the right—by rotation in relation to the dish. Because of the different wedge faces or different other raised area, a fixed, sealing closure of the dish results from one side, and closure having a defined slot or gap between the dish and the cover for gas exchange results from the other side. Different conditions for the particular cultures may thus be provided in the receptacle.

In regard to secure closing of the dish it is necessary that at least two, preferably equidistantly situated engagement means (7, 8) are provided. A stable configuration of the cover in relation to the dish and thus secure closing is provided by the provision of three equidistantly situated engagement means (7, 8), so that the cover may be situated uniformly to the dish along its circumference.

In a further advantageous way, the connection and/or positioning of the cover to the dish may be promoted in that the dish wall on the outer side and/or the cover wall on the inner side have spacers for the spacing and possibly for the clamping between cover wall and dish wall, so that a ventilation of the dish is ensured in any case if the cover is located in the open position, i.e., the position forming a gap in relation to the dish. The closed position, without the provision of a gap between the dish and the cover, is achieved if the cover wall is pressed completely on the dish or on the boundary area of the dish, namely by appropriate interaction between the engagement means of the dish and the cover.

The spacers may be concretely implemented as webs extending orthogonally from the bottom. Multiple spacers may be attached along the circumference of the dish wall in accordance with the above embodiments, it being especially advantageous if a spacer is also situated opposite to each engagement means, so that the cover wall may be inserted or plugged in between them, i.e., in the area between one engagement means and one spacer. This measure promotes secure positioning of the cover in relation to the dish.

The spacers are preferably implemented equidistantly in the dish wall and/or in the cover wall, with the provision of sufficiently many spacers ensuring uniform spacing between the cover wall and dish wall.

The handling of the receptacle according to the invention is promoted in that, on the side of the dish bottom facing away from the dish wall, a base is provided in the form of a circular ring wall, which preferably protrudes on the outer end of the boundary area in the opposite direction, and which is used for positioning and possibly stacking the dishes. This wall forms a type of pedestal for the actual dish and not only simplifies the handling, but also the storage in the empty or full state.

In a further advantageous way, it is conceivable that both the dish and also the cover, preferably having corresponding assignment, are provided with a preferably machine-readable coding (e.g., in the form of a data matrix code). The established cultures may be uniquely assigned and/or identified using such coding.

Finally, it is to be noted that the dish and the cover may be produced from glass or from preferably transparent plastic. In the case of a preferred design made of plastic, it is conceivable that the dish and the cover are produced by injection molding. Injection-molding manufacturing has the enormous advantage that all components of both the cover and also the dish may be implemented as integral components, which very significantly reduces the production costs.

BRIEF DESCRIPTION OF THE SEVERAL VIEWS OF THE DRAWINGS

There are now various possibilities for advantageously designing and refining the teaching of the present invention. For this purpose, reference is made, on the one hand, to the patent claims subordinate to claim 1 and, on the other hand, to the following explanation of a preferred exemplary embodiment of the invention on the basis of the drawing. In connection with the explanation of the preferred exemplary embodiment of the invention on the basis of the drawing, preferred designs and refinements of the teaching are also explained in general. In the figures:

DETAILED DESCRIPTION

Figure 1:
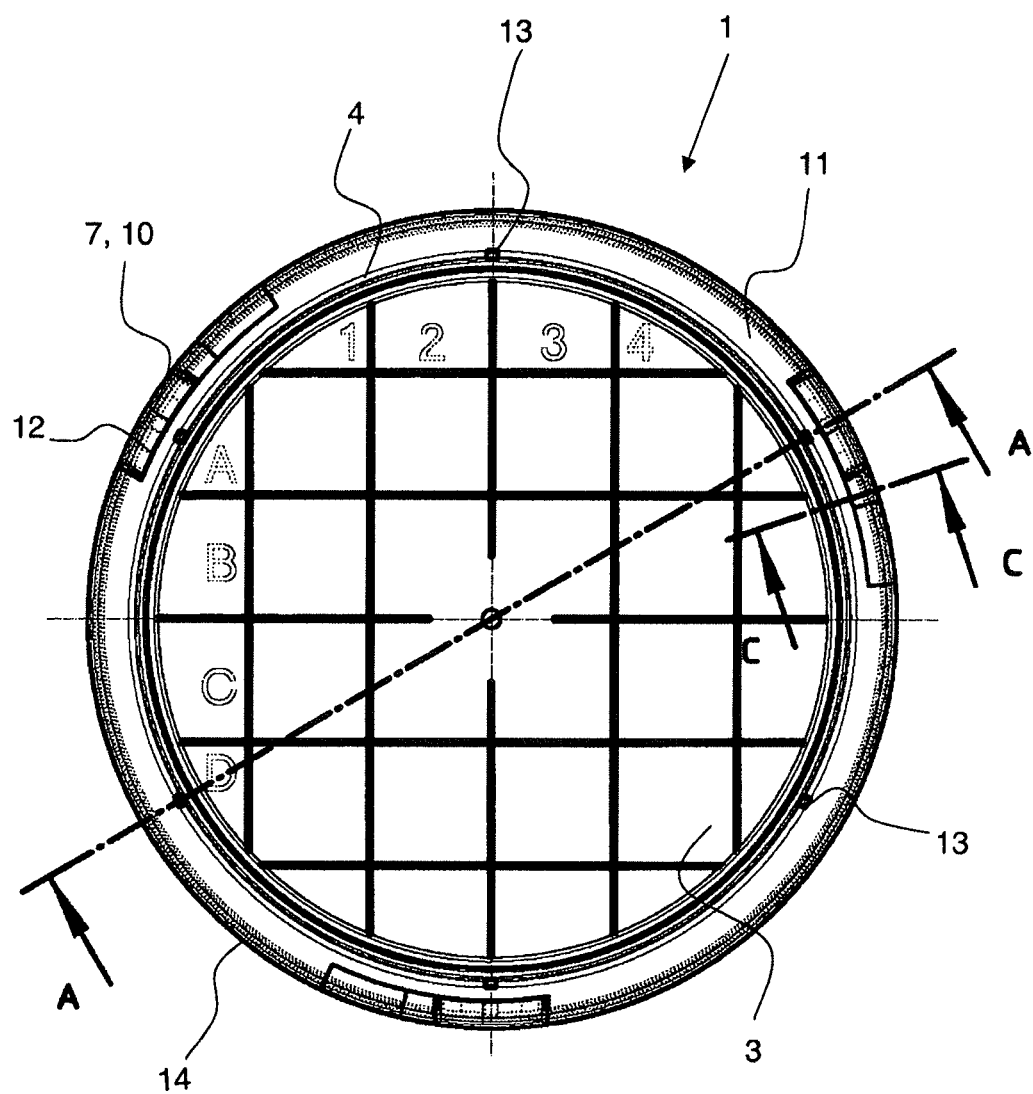
FIG. 1 shows a schematic top view of an exemplary embodiment of a dish of a receptacle according to the invention.
Figure 2A:
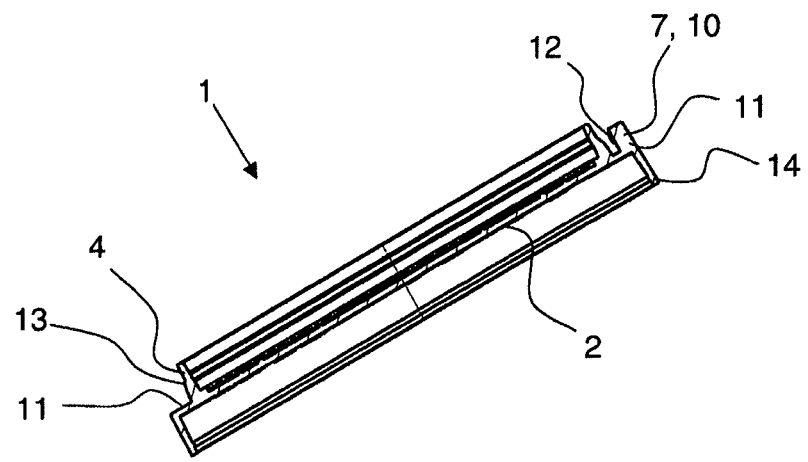
FIG. 2a shows the object from FIG. 1, partially and enlarged, in section along line A-A.
Figure 2B:
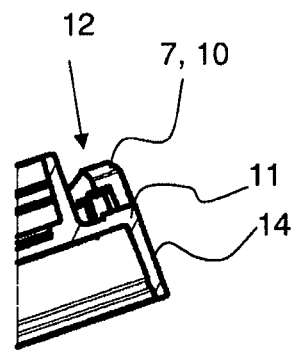
FIG. 2b shows the object from FIG. 1 in section along line C-C.

FIGS. 1 through 5 show schematic views of an exemplary embodiment of a receptacle according to the invention for accepting nutrient media, particularly for accepting cell cultures, bacteria, etc. of any type. Specifically, these are special implementations of a Petri dish.

The receptacle comprises a dish 1 and a cover 2. The cover 2 is used for closing the dish 1.

The dish 1 comprises a dish bottom 3, implemented in the form of a circular surface, and a circular ring dish wall 4, protruding from the dish bottom 3.

The cover 2 correspondingly comprises a cover bottom 5 and a cover wall 6.

Figure 3A:
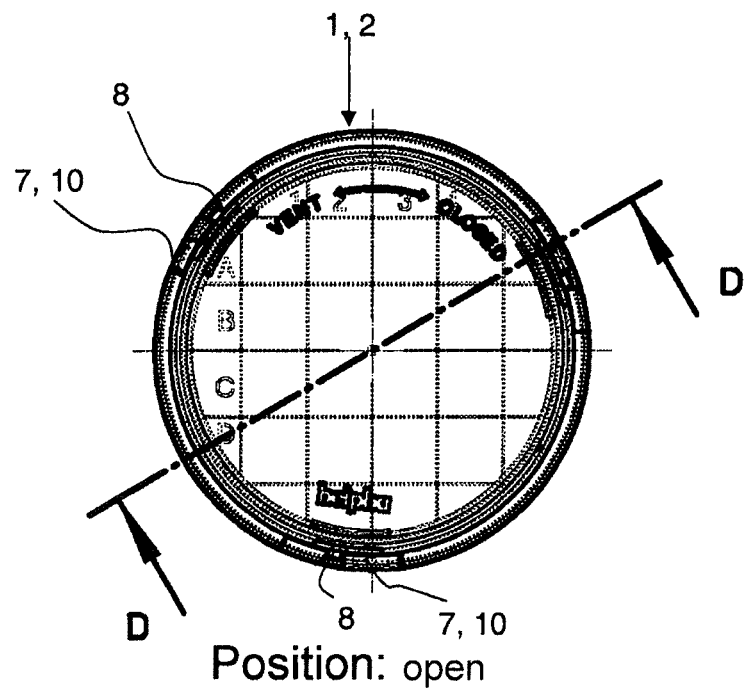
FIG. 3a shows a schematic top view of the receptacle having a dish and a cover, the cover being located in the open position.
Figure 3B:
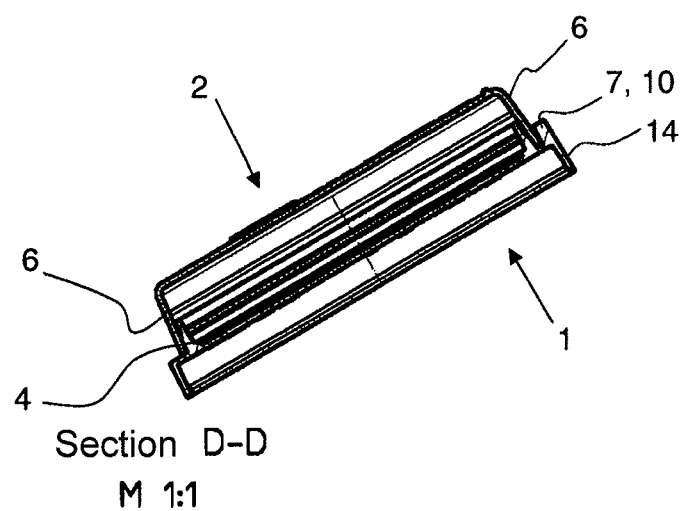
FIG. 3b shows the object from FIG. 3a in section along line D-D.
Figure 4A:
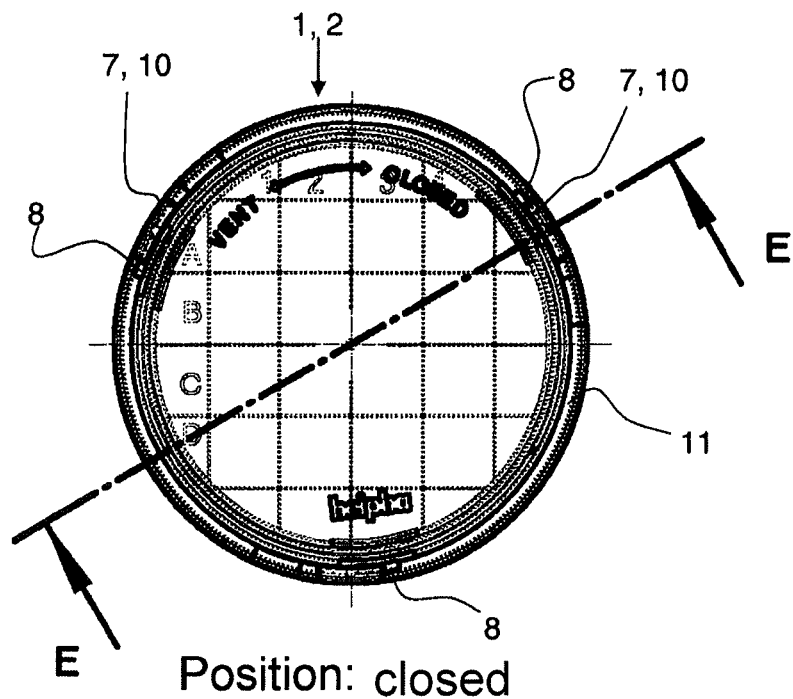
FIG. 4a shows a schematic top view of the receptacle having a dish and a cover, the cover being located in the closed position.
Figure 4B:
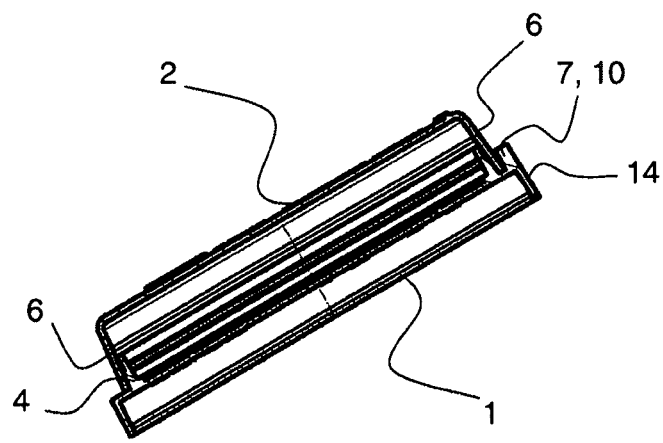
FIG. 4b shows the object from FIG. 4a in section along line E-E.
Figure 5A:
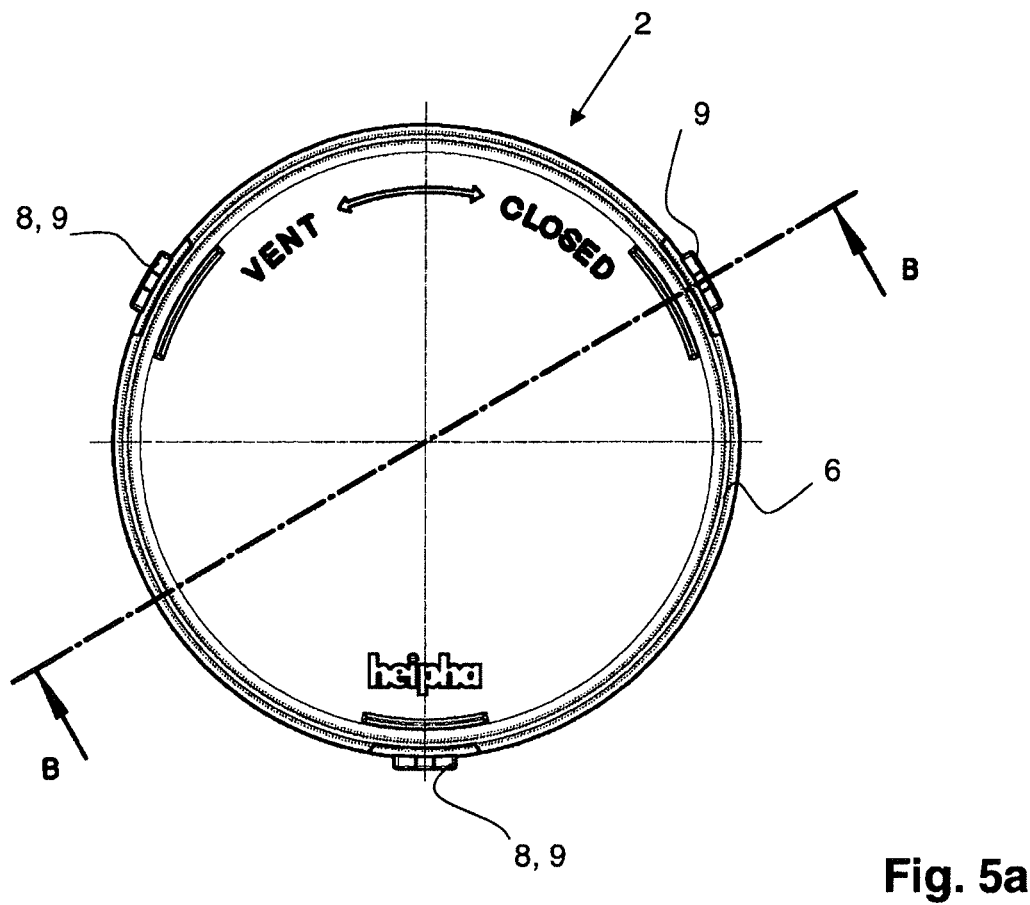
FIG. 5a shows a schematic top view of the cover of the receptacle according to the invention.
Figure 5B:
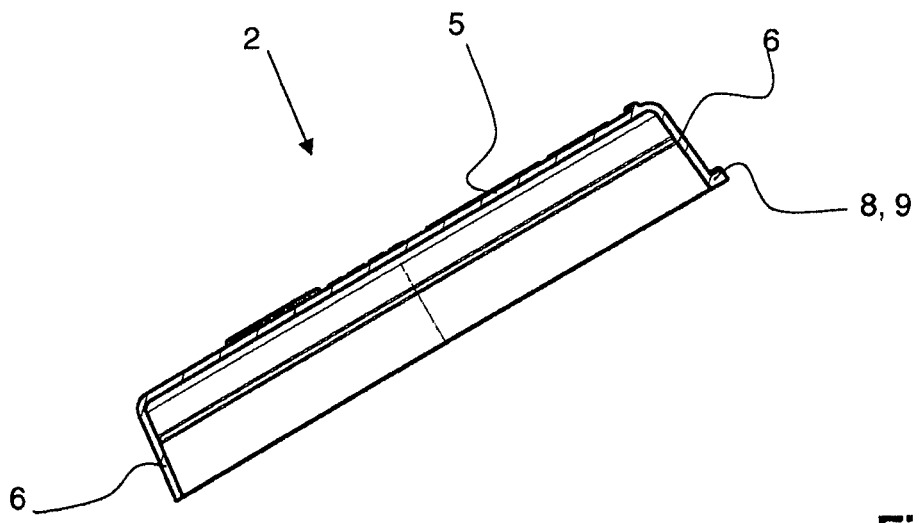
FIG. 5b shows the object from FIG. 5a in section along line B-B.

It may be seen from FIGS. 3 and 4 that the cover wall 6 has an at least slightly larger inner diameter than the outer diameter of the dish wall 4. It is thus ensured that the cover wall 6 of the cover 2 may be slipped over the dish wall 4 of the dish 1, namely to close the dish 1. Ultimately, the two parts—dish 1 and cover 2—jointly form a chamber, one part encompassing or engaging in the other part.

According to the invention, engagement means 7, 8 are assigned to the dish 1 and the cover 2, which prevent unintentional detachment of the dish 1 and the cover 2 upon mutual engagement.

Furthermore, it may be seen from the figures that the engagement means 8 assigned to the cover 2 are implemented in the meaning of catch lugs 9, which protrude orthogonally from the cover wall 6 on the free boundary of the cover wall 6. A total of three catch lugs 9 are provided along the circumference of the cover wall 6 in the exemplary embodiment selected here, at least two catch lugs 9 being necessary. In regard to the catch lugs 9, it is entirely conceivable to provide more than three catch lugs 9, namely to implement increased stability of the configuration.

The dish 1 is designed correspondingly to the design of the catch lugs 9 on the cover wall 6, namely the dish 1 has flanges 10 implemented as complementary, which are implemented like clamps. The flanges 10 extend out orthogonally from a boundary area 11 of the dish bottom and have a shoulder 12, which is responsible for the retention and/or the clamping action. The catch lugs 9 of the cover 2 may be inserted from both sides of a flange 10 into the area below the shoulder 12, differently implemented wedge faces or other protrusions being provided there—on the left and right in each case. This design measure has the result that depending on the insertion from the right or the left, at least slightly spaced or tight attachment of the cover 2 may be generated, by which an open (cf. FIG. 3) or closed (cf. FIG. 4) situation may be provided.

Furthermore, the figures show that the dish wall 4 has spacers 13 on its outer side, which are implemented along the circumference of the dish wall 4. The spacers 13 provide a type of ring gap between the inner side of the cover wall 6 and the outer side of the dish wall 4 (cf. FIGS. 3 and 4), so that if the cover 2 does not press entirely against the boundary area 11, at least slight ventilation and/or rear ventilation may be implemented. If the free boundary of the cover wall 6 presses completely against the boundary area 11, i.e., a clamping action is caused by the engagement means 7, 8, a closed situation is provided inside the receptacle (FIG. 4).

Furthermore, the figures show that the dish 1 has an integral base 14 in the form of a circular ring wall, which protrudes outward from the boundary area 11, on the side of the dish bottom 3 facing away from the dish wall 4. The base 14 is used for secure positioning, on the one hand, and for stacking the receptacle, on the other hand.

Finally, it is to be noted that the exemplary embodiment explained above is used, in addition to the figures, solely for the exemplary explanation of the claimed teaching, but does not restrict this teaching to the exemplary embodiments.

The invention claimed is:

1. A receptacle for accepting nutrient media, said receptacle comprising:
    a dish and a cover, which closes the dish, the dish and the cover each comprising a bottom (dish bottom and cover bottom), implemented in the form of a circular surface, and a circular ring wall (dish wall and cover wall), which protrudes from the bottom, and one of the walls having an inner diameter at least slightly larger than the outer diameter of the other wall, so that one wall may be slipped over the other to close the dish;
    engagement means, which prevent unintentional detachment of the dish and the cover upon mutual engagement, being assigned to the dish and the cover, and the engagement means of the dish being implemented to at least partially encompass or engage the engagement means of the cover,
    wherein the engagement means of the cover or the dish comprises a flange having two adjacent sides, with each side having a wedge face of a different height or different inclination than that of the other adjacent side, the two adjacent sides intersecting at approximately half of the length of the flange, so that the engagement means of the cover has a different clamping and sealing force depending on which side of the flange is engaged with the engagement means of the dish or the cover, and wherein the engagement means are insertable via constant sliding contact between the engagement means of the cover relative to the engagement means of the dish from either the left side or the right side of the flange.

2. The receptacle according to claim 1, wherein the engagement means are integral components of the dish and the cover.

3. The receptacle according to claim 1, wherein the engagement means are assigned to the cover wall and the dish wall.

4. The receptacle according to claim 1, wherein the engagement means are assigned to the cover wall and a peripheral outer boundary area of the dish, the outer boundary area of the dish being used as a support for the cover wall.

5. The receptacle according to claim 4, wherein the dish wall is implemented as offset inward from the outer boundary area, and the boundary area lying outside the dish wall carries the engagement means.

6. The receptacle according to claim 1, wherein the engagement means of the cover are implemented on the free boundary or near a free boundary of the cover wall, and the engagement means of the cover being able to comprise at least one catch position.

7. The receptacle according to claim 1, wherein the engagement means of the dish have at least one wedge face or other raised area for the clamping engagement with the engagement means of the cover.

8. The receptacle according to claim 1, wherein the engagement means of the dish are implemented in such a way that the engagement means of the cover may be engaged by rotating the cover in relation to the dish.

9. The receptacle according to claim 1, wherein the two-sided engagement is designed in such a way that a fixed or sealing closure is possible from one side, and a closure having a defined slot or gap for gas exchange is possible from the other side.

10. The receptacle according to claim 1, wherein at least two equidistantly situated engagement means are assigned to the dish and the cover.

11. The receptacle according to claim 1, wherein the dish wall on the outer side or the cover wall on the inner side have spacers for spacing and possibly for clamping between cover wall and dish wall, the spacers being implemented as webs extending orthogonally from the bottom or one spacer being able to be implemented opposite to one engagement means.

12. The receptacle according to claim 11, wherein the spacers are implemented equidistantly in the dish wall or in the cover wall.

13. The receptacle according to claim 1, wherein a base is implemented on the side of the dish bottom facing away from the dish wall in the form of a circular ring wall, which is used for positioning and possibly stacking the dish.

14. The receptacle according to claim 1, wherein the dish or the cover is provided with a machine-readable coding.

15. The receptacle according to claim 1, wherein the dish and the cover are produced from transparent plastic, the dish and the cover being produced by injection molding.

16. The receptacle according to claim 1, wherein the cover wall has an inner diameter at least slightly larger than the outer diameter of the dish wall.

17. The receptacle according to claim 5, wherein the boundary area carrying the engagement means lies entirely outside the dish wall.

18. The receptacle according to claim 6, wherein the engagement means protrude outward orthogonally from the cover wall.

19. The receptacle according to claim 10, wherein three equidistantly situated engagement means are assigned to the dish and the cover.

20. The receptacle according to claim 1, wherein the engagement means of the dish are selected from the group consisting of clamps, flanges, threads, and a combination thereof.

21. The receptacle according to claim 6, wherein the engagement means of the cover are selected from the group consisting of catch lugs, flanges, threaded parts, and combinations thereof.

22. The receptacle according to claim 13, wherein the base protrudes on an outer end of a boundary area in an opposite direction.

* * * * *